(12) United States Patent
Ikeda et al.

(10) Patent No.: US 7,795,032 B2
(45) Date of Patent: Sep. 14, 2010

(54) METHODS FOR PROLIFERATING CARDIOMYOCYTES AND RECOMBINANT VECTORS THEREFOR

(76) Inventors: Masaaki Ikeda, 12-28, Sendagi 3-chome, Bunkyo-ku, Tokyo (JP) 113-0022; Mimi Adachi, 2-18-1-307, Higashi-Nakano, Nakano-ku, Tokyo (JP) 164-0003

( * ) Notice: Subject to any disclaimer, the term of this patent is extended or adjusted under 35 U.S.C. 154(b) by 0 days.

(21) Appl. No.: 10/713,008

(22) Filed: Nov. 17, 2003

(65) Prior Publication Data
US 2005/0208659 A1 Sep. 22, 2005

Related U.S. Application Data

(63) Continuation of application No. PCT/JP01/08208, filed on Sep. 21, 2001.

(30) Foreign Application Priority Data

May 17, 2001 (JP) ............................. 2001-148266

(51) Int. Cl.
*C12N 15/00* (2006.01)
*C12N 15/86* (2006.01)
*A01N 43/04* (2006.01)
(52) U.S. Cl. ....................... 435/455; 435/456; 514/44 R
(58) Field of Classification Search .................. 435/455, 435/456; 514/44, 44 R
See application file for complete search history.

(56) References Cited

U.S. PATENT DOCUMENTS 6,180,763 B1 * 1/2001 Sherr et al. .................. 530/413
7,256,256 B1 * 8/2007 Paterson et al. ............. 530/326

OTHER PUBLICATIONS

Brooks et al. The cell cycle and drug discovery: the promise and the hope. Drug Discovery Today (1999) vol. 4, No. 10, pp. 455-464.*
Pagano et al. Wagging the dogma: tissue-specific cell cycle control in the mouse embryo. Cell (2004) vol. 118, pp. 535-538.*
Verma et al. Gene therapy-promises, problems and prospects, Nature, 1997, vol. 389, pp. 239-242.*
Marshall, E. Gene therapy's growing pains. Science, 1995, vol. 269, p. 1050-1055.*
Juengst, E.T. What next for human gene therapy? British Medical Journal, 2003, vol. 3326, pp. 1410-1411.*
Rubanyi, G.M. The future of gene therapy. Molecularr Aspects of Medicine, 2001, vol. 22, pp. 113-142.*
Eck et al. Goodman and Gilman's The pharmacological basis of therapeutics, 1996, McGraw-Hill, NY, 9th Edition, Chapter 5, pp. 77-100.*
Ross et. Gene therapy in the United States: A five-year staus report. Human Gene therapy, 1996, vol. 7, pp. 1781-1790.*
Johnson et al. The utility of naimal models in hte preclinical study of interventions to repvent human coronary artery restenosis: analysis and recommendations. Thromb Haemost (1999) vol. 81, pp. 835-843.*
Patel et al (Safety of Direct Myocardial Administration of an Adenovirus Vector Encoding Vascular Endothelial Growth Factor 121, Human Gene Therapy .10:1331-1348).*
Tamamori-Adachi et al (Expression of cyclin D1 and CDK4 causes hypertrophic growth of cardiomyocytes in culture: a possible implication for cardiac hypertrophy. Biochemical and Biophysical Research Ocmmunications, 2202. 296:274-280).*
Nicol et al (FromThe SarcomereTo the Nucleus: Role of Genetics and Signaling in Structural Heart Disease, Annual Review of Genomics and Human Genetics, 2000. 1: 179-223).*
Soonpaa et al (Cyclin D1 overexpression Promoter Cardiomyocyte DNA synthesis and Multinucleation in Transgenic Mice. Journal of Clinical Investigation, 1997: 99(11):2644-2654).*
Gojo et al. Ann. R. Coll. Surg. Engl. 84:297-301; 2002.*
Davey, J. et al., "Identification of the Sequence Responsible for the Nuclear Accumulation of the Influenza Virus Nucleoprotein", *Cell* (1985), vol. 40, pp. 667-675.
Kalderon, D. et al., "Sequence requirements for nuclear location of simian virus 40 large-T antigen", *Nature* (1984), vol. 311, pp. 33-38.
Kirshenbaum, L. A. et al., "Adenovirus E1A Represses Cardiac Gene Transcription and Reactivates DNA Synthesis in Ventricular Myocytes, via Alternative Pocket Protein- and p300-binding Domains", *The Journal of Biological Chemistry* (1995), vol. 270, pp. 7791-7794.
Kirshenbaum, L.A. et al., "Human E2F-1 Reactivates Cell Cycle Progression in Ventricular Myocytes and Represses Cardiac Gene Transcription", *Developmental Biology* (1996), vol. 179, pp. 402-411.
Leone, G. et al., Myc and Ras collaborate in inducing accumulation of active cyclin E/Cdk2 and E2F, *Nature* (1997), vol. 387, pp. 422-426.
Lew, D. et al., "Isolation of Three Novel Human Cyclins by Rescue of G1 Cyclin (Cin) Function in Yeast", *Cell* (1991), vol. 66, pp. 1197-1206.

(Continued)

*Primary Examiner*—Fereydoun G Sajjadi
(74) *Attorney, Agent, or Firm*—Hunton & Williams LLP

(57) ABSTRACT

Terminal differentiated cells are proliferated by introducing a cyclin and a cyclin dependent kinase into the nucleus of terminal differentiated cells, and then cultivating or holding the cells. A method for proliferating terminal differentiated cells comprising adding a nucleotide sequence coding for a nuclear localization signal to at least one of a cyclin gene and a cyclin dependent kinase gene, and introducing each of the genes to terminal differentiated cells in vitro, and then cultivating the cells, or introducing each of the genes directly to terminal differentiated cells in vivo is provided. The cyclin is a cyclin that can activate CDK4 or CDK6, and the cyclin dependent kinase is a cyclin dependent kinase that is activated by D-type cyclin. The invention also provides a recombinant vector used for such a method or a pharmaceutical composition comprising the vector.

21 Claims, 7 Drawing Sheets

OTHER PUBLICATIONS

Matsunshime, H. et al., "Colony-Stimulating Factor 1 Regulates Novel Cyclins during the G1 Phase of the Cell Cycle", *Cell* (1991), vol. 65, pp. 701-713.

Mizuguchi, H. et al., "Efficient Construction of a Recombinant Adenovirus Vector by an Improved In Vitro Ligation Method", *Human Gene Therapy* (1998), vol. 9, pp. 2577-2583.

Robbins, J. et al., "Two Interdependent Basic Domains in Nucleoplasmin Nuclear Targeting Sequence: Identification of a Class of Bipartite Nuclear Targeting Sequence", *Cell* (1991), vol. 64, pp. 615-623.

Scholzen, T. et al., "The Ki-67 Protein: From the Known and the Unknown", *Journal of Cell Physiology* (2000), vol. 182, pp. 311-322.

Soonpaa, M. H. et al., "Cyclin D1 Overexpression Promotes Cardiomyocyte DNA Synthesis and Multinucleation in Transgenic Mice", *J. Clin. Invest.* (1997), vol. 99, pp. 2644-2654.

Tamamori, M. et al., "Essential roles for $G_1$ cyclin-dependent kinase activity in development of cardiomyocyte hypertrophy", *the American Physiological Society* (1998), pp. H2036-2040.

Gavin Brooks et al., Arresting developments in the cardiac myocyte cell cycle: Role of cyclin-dependent kinase inhibitors, Cardiovascular Research (1997), vol. 39, pp. 301-311.

Charles J. Sherr et al., CDK inhibitors: positive and negative regulators of G1-phase progression, Genes & Development, (1999), vol. 13, pp. 1501-1512.

Davis, J., et al., "Designing Heart Performance by Gene Transfer", Physiological Reviews, vol. 88, pp. 1567-1651, Oct. 2008.

Muller, O., et al., "Targeting the Heart With Gene Therapy-Optimized Gene Delivery Methods", Cardiovascular Research, vol. 73, pp. 453-462, Revision Accepted Sep. 2006.

\* cited by examiner

METHODS FOR PROLIFERATING CARDIOMYOCYTES AND RECOMBINANT VECTORS THEREFOR

CROSS REFERENCED RELATED APPLICATION

This application is a continuation application a National Stage of International Application No. PCT/JP01/08208, filed Sep. 21, 2001, and claimed priority to Japanese Patent Application No. 2001-148266 filed May 17, 2001 is hereby incorporated by reference in its entirety.

TECHNICAL FIELD

The invention relates to methods for proliferating terminal differentiated cells and recombinant vectors therefor. More specifically, the invention relates to methods and the like for proliferating terminal differentiated cells by using cyclins and cyclin dependent kinases.

BACKGROUND ART

The eucaryotic cell cycle is regulated by cyclin dependent kinases (CDKs). These are phosphoenzymes (kinases), which are only activated after binding with a cyclin subunit, and do not have the activity by themselves. Various processes in cell cycles, such as replication and introduction to mitosis, are regulated by different CDKs. The expression levels of CDKs are generally consistent and the activities of CDKs are dependent on the expression levels of cyclins. Cyclins are transiently expressed at required stages in the cell cycle and activate CDKs.

Additionally, CDK activity is also regulated by a group of inhibitory factors, called CDK inhibitors. These inhibitors are roughly classified into two groups based their primary structure and their specificity for inhibiting CDK, particularly, the INK4 family (Inhibitor of CDK4), and the CIP/KIP family (CDK interacting protein/kinase inhibitory protein). Comparing the progression of the cell cycle to driving an automobile, CDKs play a role of accelerator, and CDK inhibitors play the role of a brake. The progression of cell cycle is determined by the concerted regulation of both of the accelerator and the brake.

When quiescent cells enter the cell cycle, D-type cyclins are expressed from the middle to late G1 phase in response to the mitogenic stimulation. Ras/Raf-1/MAPK accelerate the transcription of the genes coding for D-type cyclins, and PI3K (phosphatidylinositol 3-kinase)/Akt (protein kinase B) repress the degradation of the gene products. CDK4 and CDK6 bind to D-type cyclins, the assembled proteins enter the cell nucleus where they must be phosphorylated by CAK (CDK-activating kinase) to become active. D-type cyclins have been reported to be a cytoplasmic sensor for stimulation signals, i.e., their expression is induced in response to extracellular growth factors, and they play a role for transferring the signal to CDK2 and CDC2 which progress the cell cycle. It is also reported that D-type cyclin/CDK4, 6 have two roles for cell cycle progression. One is the role of canceling the growth inhibitory effect of RB (the retinoblastoma protein) through phosphorylation and another is trapping (sequestering) CIP/KIP. When CIP/KIP exists alone in the cell, the activity of CDK2 appeared in G1 anaphase, has been inhibited. It is speculated that D-type cyclin/CDK reduces the activity of such inhibitors as CIP/KIP to inhibit CDK2 by associating therewith.

In G1 phase of cell cycle, the target of CDK is RB. RB is known as to associate with many proteins, especially with a key molecule, transcription factor E2F. E2F regulates the transcription of the genes which are necessary for progression of the cell cycle and DNA replication. For example, it activates the transcription of cyclin E. Thus, E2F plays an important role for initiation of the S phase through the function of cyclin E/CDK2. The non-phosphorylated RB binds with E2F strongly, and represses the DNA replication by E2F. When RB is phosphorylated CDK, the phosphorylated RB loses the function to repress E2F, and becomes inactive. [Recently, it has been reported that the homologous proteins of RB and E2F. They are called the RB family and the E2F family respectively.] As a result, it has been revealed that the progression of the cell cycle from G1 to the S phase is a highly regulated process by both the RB and E2F family proteins. Further, this RB-E2F pathway was revealed to be related to many biological events such as cell differentiation, malignant transformation and apoptosis. For example, inactivation of RB and the like causes the abnormal regulation of cell cycle, and leads to the malignant transformation of the cell. A number of these genes, which regulate the cell cycle, are reported to be cancer suppressor genes.

On the other hand, it is known that terminal differentiated cells such as cardiomyocytes and nerve cells withdraw from the cell cycle and take on the special state called the stationary phase (G0 phase). Cardiomyocytes, one of these terminal differentiated cells loses proliferative activity soon after birth. Thus, the necrosis or loss of cardiomyocytes by infarction or dilated cardiomyopathy leads to failure of regeneration of cardiomyocytes. Thereafter, there are a lot of cases for severe heart failure and death resulting in a high mortality rate of these cardiac diseases. Although it has been thought that cardiomyocytes are arrested at G0 phase and the cell cycle does not proceed, recent studies suggest that cardiomyocytes have the regulatory mechanisms of the cell cycles.

For example, adenovirus transforming gene product E1A promotes transcription of E2F dependent genes by interacting with the RB, and induces cellular DNA synthesis. A study of whether E1A releases E2F in cardiomyocytes and induces DNA synthesis and dedifferentiation using rat neonatal cultured cardiomyocytes showed E1A alone did not clearly induce the DNA synthesis but leads to apoptosis. In the presence of E1B, E1A is reported to induce DNA synthesis in cardiomyocytes (Kirshenbaum, L. A. et al., The Journal of Biological Chemistry 270, 7791-7794 (1995)).

As a result of using E2F adenovirus, it has been reported that E2F represses the expression of myocardial specific genes in cardiomyocytes, and induces DNA synthesis (Kirshenbaum, L. A. et al., Developmental Biology 179, 402-411, (1996)).

On the other hand, the transgenic mouse, in which a wild type cyclin D1 without nuclear localization signals was overexpressed, showed elevated expression levels of CDK4, as well as, DNA synthesis in cardiomyocytes, however, it was reported that abnormal multinucleated cells were increased (Soonpaa, M. H et al., Clin. Invest. 99, 2644-2654, (1997)).

From such a line of research, DNA synthesis is observed and progression of cell cycles is suggested in cardiomyocytes, however, subsequent cell division or increase of cell numbers has not been reported. Thus, any method for substantially proliferating cardiomyocytes without induction of apoptosis is not known.

Recently, for the purposes of organ transplantation or treatment of leukemia and the like, the regeneration medical technology to produce desired kinds of cells using multipotent cells called as embryonic stem (ES) cells have been studied.

However, because ES cells are produced by disrupting an embryo that has a potential to grow into a fetus, there are many ethical resistances to the research.

In view of the above problems, the invention is directed a method for proliferating terminal differentiated cells, which is applicable for the development of cardiac regenerating therapy and self-transplantation of well-differentiated organs such as cardiomyocytes. It is a further object of the invention to provide a recombinant vector that can be used for above method, or a pharmaceutical composition thereof.

DISCLOSURE OF THE INVENTION

To solve the above problems, the inventors investigated the mechanism of cell cycle regulation in the terminal differentiated cells, especially, the role of cyclin/CDK in cardiomyocytes induced by mitogenic stimuli. As a result, it was found that the D-type cyclin/CDK4 induced by mitogenic stimuli remained in the cytoplasm of cardiomyocytes, and did not enter the cell nucleus, whereby neither phosphorylation of RB nor activation of cyclin E/CDK2 took place. Therefore, the inventors constructed adenovirus vectors with a cyclin D1 gene attached and a nuclear localization signal (NLS), as well as a CDK4 gene respectively, and introduced these adenovirus vectors into cultured cardiomyocytes. These viruses caused not only expression of cyclin D1/CDK4 in the nucleus and RB phosphorylation, but also proliferation of cardiomyocytes.

A first aspect of the invention, provides a method for proliferating terminal differentiated cells comprising, introducing a cyclin and a cyclin dependent kinase into the nucleus of terminal differentiated cells, and then cultivating or holding said cells.

A preferred embodiment for introducing the cyclin and the cyclin dependent kinase into the nucleus of terminal differentiated cells, provides a method comprising the steps of adding a nucleotide sequence coding for a nuclear localization signal to at lease one of a cyclin gene and a cyclin dependent kinase gene; introducing each of the genes to terminal differentiated cells in vitro, and then cultivating the cells, or introducing each of said genes directly to terminal differentiated cells in vivo.

In a further preferred embodiment, the cyclin is a cyclin that is capable of activating CDK4 or CDK6, for example, preferably mammalian cyclin D1, D2 and D3. The cyclin dependent kinase is a cyclin dependent kinase that is activated by D-type cyclin, for example, preferably CDK4 and CDK6.

In another preferred embodiment, the terminal differentiated cells are cardiomyocytes, nerve cells, kidney cells, or pancreatic cells.

In a still further preferred embodiment, the cyclin gene and the cyclin dependent kinase gene are transferred to the terminal differentiated cells using an adenovirus vector.

A second aspect of the invention, provides a recombinant vector comprising a cyclin gene comprising a nucleotide sequence coding for a nuclear localization signal (NLS; a signal peptide having a function of transporting the protein into the nucleus), or a cyclin dependent kinase gene comprising a nucleotide sequence coding for a NLS. The recombinant vector may comprise both a cyclin gene and a cyclin dependent kinase gene, if only at least one of said genes is (are) attached with a nucleotide sequence coding for a nuclear localization signal.

In a preferred embodiment, the cyclin is a cyclin that is capable of activating CDK4 or CDK6, and the cyclin dependent kinase is a cyclin dependent kinase that is activated by cyclin D1, D2 or D3.

In a further preferred embodiment, the recombinant vector further comprises an adenovirus vector, and the nucleotide sequence of said nuclear localization signals is that derived from large T antigen of SV40. In particular, said sequence is recommended to encode for triplicate nuclear localization signals derived from large T antigen of SV40.

A third aspect of the invention, provides a mammalian cell or tissue that was proliferated by any one of the methods in the above first aspect.

Further, a fourth aspect of the invention, provides a pharmaceutical composition for proliferating terminal differentiated cells or tissues, comprising an effective amount of any one of the recombinant vectors in the above second aspect of the invention.

In the preferred embodiment, the pharmaceutical composition provides a method for treating cardiopathy in a human patient comprising directly introducing into myocardium of the patient the virus vector expressing a cyclin gene and a cyclin dependent kinase gene attached with a nucleotide sequence coding for a nuclear localization signal to at lease one of said genes, and proliferating said myocardium of the patient.

BRIEF DESCRIPTION OF THE INVENTION

FIG. 1 shows the western blot analysis of the expression of cyclin D1 and the phosphorylation of RB in cardiomyocytes stimulated by various growth stimuli. ppRB: phosphorylated RB protein, pRB: RB protein.

FIG. 2 shows the western blot analysis of the expression of D-type cyclin and CDK4 in cytoplasmic extract or nucleic extract in cardiomyocytes stimulated by various growth stimuli. RB:RB protein FIG. 3 are photographs of subcellular localization of cyclin D1 induced by various stimuli in cardiomyocytes analyzed by immunofluorescence staining with the mouse monoclonal anti-sarcomeric actin antibody.

Figure 11A:
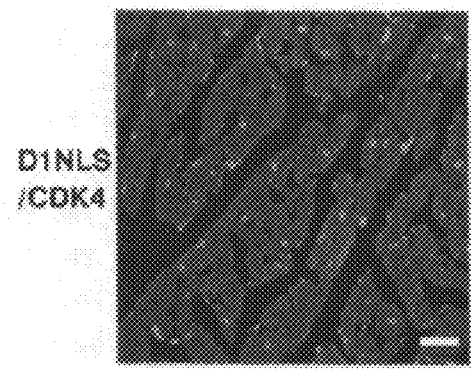
Figure 11B:
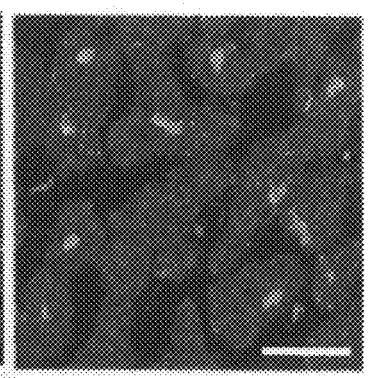
Figure 11C:
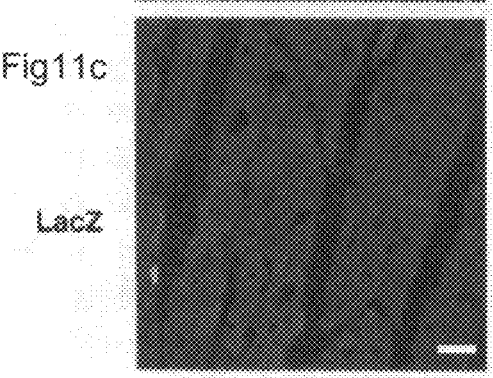

FIG. 11 shows the visualized views of expressed proteins by immunofluorescence staining of heart tissue section after infection of recombinant adenovirus comprising D1NLS/CDK4 (FIG. 11a and FIG. 11b) or lacZ gene (FIG. 11c) in rat cardiomyocytes in vivo. Red, sarcomeric actin; green, Ki-67. Bar, 20 μm.

In each of the above Figs., the symbols mean as follows.

+: addition of each of the growth factors or infection of each of the recombinant adenoviruses.

—: no addition of each of the growth factors or non-infection of each of the recombinant adenoviruses.

Preferred Embodiments (Cyclins and Cyclin Dependent Kinases)

Mammalian D-type cyclins consists of 3 kinds of subtypes (D1, D2, D3). They are expressed during from middle to late G1 phase, and activate CDK4 and CDK6 by binding therewith. They promote G1-to-S phase progression by phosphorylating predominantly RB protein. Although cyclin D1 is localized in the cell nucleus during G1 phase, it is exported to the cytoplasm by the phosphorylation of cyclin D1 at threonine 286 by glycogen synthase kinase 3β (GSK-3β), which leads to degradation of cyclin D1 by proteasome. Various functions of cyclin D1/CDK4 except for the cell cycle, such as regulation of differentiation of muscle through the inhibition the transcription factor MyoD, and activation of ER (estrogen receptor) by binding therewith in the epithelial cell of mammary gland, have been reported.

The invention relates to a method for proliferating terminal differentiated cells through the progression of the cell cycle by introducing such cyclins and cyclin dependent kinases into the nucleus of terminal differentiated cells. As for the method of introducing these proteins into cell nucleus, there is a physical injection method such as microinjection, however, it is preferable to use the gene transfer method in view of efficiency of gene transfer. Any cyclin that can activate CDK4 and CDK6 is preferably introduced, for example, the above 3 kinds of subtypes (cyclin D1, D2, D3). Any cyclin dependent kinase which is activated by D-type cyclin is preferably introduced, for example, CDK4 and CDK6.

(Preparation of Terminal Differentiated Cells)

The terminal differentiated cells used for the methods of the invention can be isolated from a living subject and cultured by various methods. The term "terminal differentiated cells" means the cells staying in G0 phase of cell cycles without a cell division throughout an individual life, such as cardiomyocytes, nerve cells, kidney cells, pancreatic cells and the like. For example, when the cultured cardiomyocytes from 1 to 2-day post-natal rats are analyzed by cell cycle assay such as flow cytometry, it is confirmed that more than 90% of the cells are G0/G1 phase within 24 hours after cultivation. In addition, even when the growth stimulation such as serum is added, the cells do not enter the S phase (Claycomb, W. C., Trends Cardiovascular Medicine 2, 231-236, (1992)).

Similarly, central nervous cells, especially brain cells, have completed division at the fetal stage, therefore, brain disorders after birth are difficult to cure. When kidney cells are impaired, treatments such as artificial dialysis are often necessary due to the loss of regeneration. Pancreatic cells produce a lot of digestion enzymes and gastrointestinal hormones. When the β cell was impaired, insulin secretion was inhibited due to the loss of regeneration thereof. Thus, this is known to be a cause of diabetes. In the present invention, these terminal differentiated cells can be proliferated by applying the method of the invention in vitro, or in vivo, and then cultivating or holding said cells.

(Construction of the Recombinant Vectors)

D-type cyclin genes and cyclin dependent kinase genes have been cloned from humans and various other organisms, and their sequences have been reported. For example, the nucleotide sequence of mouse cyclin D1 gene is described in Matsushime, H. et al., Cell, 65, 701-713, (1991), and registered in GenBank (Accession No. M64403). In addition, human cyclin D1 gene is described in Lee, D. et al., Cell, 66, 1197-1206, (1991) and the like. Human CDK4 is a protein consisting of 303 amino acid residues, and the cDNA sequence encoding thereof is registered in GenBank (Accession No. M14505). Further, these genes can be obtained by polymerase chain reaction (PCR) with specific primers for desired gene and mammalian genomic DNA as a template.

To introduce proteins encoded in these genes into the nucleus of terminal differentiated cells, it is necessary to import the proteins synthesized in the cytoplasm into the nucleus. For this purpose, nucleotide sequences encoding a nuclear localization signal is attached to at least one of the above genes, preferably a cyclin gene. At present, 3 kinds of nuclear localization signals are known. All of these sequences have a consensus sequence referred to as a motif.

The first is a type of sequence that hardly has a basic amino acid such as lysine and arginine and the like. Although the examples of this type of motif is very small in number, there is a nuclear localization signal of the nucleoprotein of influenza virus (AAFEDLRVLS: SEQ ID No. 1) (Davy, J. et al., Cell, 40, 667-675, (1985)). The second is a type of sequence that has a number of basic amino acids. There are a lot of examples of this type of motif, for example, a nuclear localization signal of SV40 large T antigen (PPKKKRKV: SEQ ID No. 2) (Kalderon, D. et al., Nature, 311, 33-38, (1984)). The third is a type of sequence that basic amino acids form the cluster approximately 10 amino acid apart, and referred to as Bipartite type nuclear localization signal. There are also a lot of examples of this type of motif, for example, a nuclear localization signal of the nucleoplasmin of Xenopus laevis (KRPAATKKAGQAKKKK: SEQ ID No. 3) (Robbins, J. et al., Cell, 64, 615-623, (1991)).

The nucleotide sequence coding for the nuclear localization signal is attached to at least one D-type cyclin gene and cyclin dependent kinase gene which is activated by cyclin. The two proteins expressed by these genes form the complex in the cytoplasm. Therefore, if one of these proteins, preferably cyclin has a nuclear localization signal, complex is capable of passing through the nuclear membrane. The recombinant vector containing the nucleotide sequences coding for these nuclear localization signals, and used for cloning a DNA from which the expressed protein is imported to nucleus, can be easily obtained. For example, the expression plasmid pEF/myc/nuc having a nuclear localization signal of SV40 large T antigen is purchased from Invitrogen Corp.

Vectors may be derived, for example, from virus as adenovirus, adeno associated virus, retrovirus, vaccinia virus, chick poxvirus and papovavirus as SV40, and the like.

Adenovirus vectors used in the preferred embodiment of the invention can be prepared by homologous recombination method (Miyake, S. et al., Proc. Natl. Acad. Sci. USA, 93, 1320, (1996)) and in vitro ligation method (refer to Mizuguchi, H. et al., Gene Ther. 9, 2577-2583, (1998)) using human embryonic kidney cell line 293 (HEK293) or E. coli. Adenovirus is one of DNA viruses having a linear double stranded DNA genome, and human adenovirus antigen type 5 (AD5) and human adenovirus antigen type 2 (AD2) are most well-studied. Non-replicable adenovirus vectors can be prepared by deleting most of the early gene 1 (E1) and the early gene 3 (E3) of these wild type adenovirus. Several kb exogenous DNA can be inserted into these viruses without any harmful effect on the virion morphogenesis. The recombinant adenovirus deletes the transcription factor E1 gene, however, the inserted target genes can be expressed predominantly by the transcription unit specific for the inserted gene, without any dependence on the growth of the target cells or presence of other virus genes. For constructing these expression systems, the Adenovirus Expression Vector Kit (Takara) is commercially available.

(Gene Transfer and Cultivation of the Cells)

Any conventional method of gene transfer, which is known previously, can be used for introducing genes. For example, there are tansfection methods with recombinant DNA using calcium phosphate or liposome, and transduction methods using various viruses such as retrovirus. The retrovirus used for the transduction usually infects the specific cell, and integrates the genetic information to the cellular DNA itself, however, it may infect more than two kinds of cells. The expression of the introduced genes may be transient or constitutive by integrating to the chromosomal DNA of the recipient cells. It is preferable to use the recombinant adenovirus vectors for efficient transduction and high level expression of the introduced genes. The introduction of the genes by adenovirus is one of the most powerful methods for introducing genes into mammalian cells, and can be used for the gene transfer to actually all kinds of human cells and a number of non-human cells. In addition, the infection by adenovirus is not dependent on cell cycles, therefore, the adenovirus vector can be used for expressing the genes in various primary culture cells or transformed cell lines. In particular, it can introduce the genes effectively even in the cells that do not synthesize DNA nor undergo cell division such as terminal differentiated cells. After the infection, a number of cells receive a plural of recombinant DNA copies, thus the introduced genes are expressed in high level transiently. Further, the adenovirus DNAs are not integrated to the cellular genome in general, but remain as episomes. Accordingly, it is an advantage that the gene transfer using adenoviruses scarcely causes mutated errors at the random integration of heterogeneous DNA into the host cell genome.

In the present invention, to express both genes of D-type cyclins and cyclin dependent kinases that are activated by said cyclins, these genes can be infected by the same recombinant virus or separate recombinant viruses. When more than two kinds of viruses are used for co-infection, these viruses can be infected simultaneously or separately after a set period of time. In the present invention, the amount of infected virus is adjusted preferably approximately 100/cell (MOI=100) using for example $10^9$ to $10^{11}$/ml virus stock solution. The efficiency of gene transfer by co-infection of two different types of adenovirus is also high, and the survival rate of the cell after co-infection can be high. The virus amount (titer) can be easily measured by plaque assay.

The terminal differentiated cells of which a D-type cyclin and a cyclin dependent kinase which can be activated by said cyclin are expressed in the nuclei, are proliferated by cultivating according to the conventional methods previously known. The preferable method of cultivating said cells can be selected from the group consisting of microtiter plate, static culture in petri-dish or flask, rolling bottle culture, micro carrier culture and the like, depending on the kind of said cells. For example, cardiomyocytes can be cultivated in minimum eagles medium (MEM) and the like, supplemented with growth factors such as 5 to 20% fetal calf serum and the like, in the presence of 5% carbon dioxide gas, at 37° C. Nerve cells, kidney cells and pancreatic cells can be also cultivated by the same method. Various culture media for the growth of each cell in the most preferable condition are developed and purchased, for example, RPMI1640, CMRL1066 and the like. These various culture media are available from the market such as Flow Laboratories, Gibco and the like.

In the present invention, the genes are also introduced in vivo, for example, they are directly introduced into mammalian terminal differentiated cells or tissues and held said cells or said tissues in vivo for proliferation. Here, the term "hold" means to maintain said cells or said tissues in the physiological conditions such as body temperature and bloodstream without loss of physiological function thereof.

(Proliferated Cells and Tissues)

The present invention also relates to cells and tissues that were proliferated by the method of the present invention. For example, a D-type cyclin gene attached with nuclear localization signals and a cyclin dependent kinase gene which can be activated by said cyclin are introduced to the terminal differentiated cells extirpated from patients by the aforementioned method, and cultured to proliferate. These proliferated cells and tissues can be used for regenerating the necrotic cells or tissues by injection into said patients. Specifically, cardiomyocytes, nerve cells, kidney cells and pancreatic cells can be transplanted to the patients.

(Pharmaceutical Compositions to Regenerate the Terminal Differentiated Cells and/or Tissues)

The recombinant vectors of the present invention can be used for the prevention or the treatment of diseases. When the specific cells or tissues are injured, the necrotic tissues or organs can be repaired or recruited by proliferating such terminal differentiated cells or tissues to which the pharmaceutical compositions comprising an effective amount of the recombinant vector of the present invention were injected. For example, the recombinant vectors of the present invention can be used for the treatment of cardiac infarction or dilated cardiomyopathy. In this case, the pharmaceutical compositions comprising the above recombinant vectors can be directory injected to the heart of the patient to proliferate the patient's cardiac muscle (cardiomyocytes).

EXAMPLES

The present invention is explained in more detail by reference to the following examples which use cardiomyocytes as a terminal differentiated cell. Although these examples show embodiments in which rat cardiomyocytes are proliferated in vitro, they do not restrict the scope of the present invention.

Example 1

Preparation of Recombinant Adenoviruses

1) Preparation of Ad-CDK4

The plasmid pCMV-CDK4 was provided by Dr. Sander van den Heuvel (Massachusetts General Hospital Cancer Center, van den Heuvel et al., Science, 262, 2050-2054 (1993)). The plasmid pCMV-CDK4 contained a mouse CDK4 gene. The recombinant Ad-CDK4 was constructed from pCMV-CDK4 by using Adenovirus Expression Vector Kit (Takara, Tokyo, Japan, Code No. 6150) as follows.

pCMV-CDK4 was digested by BamHI to isolate an approximately 920 bp DNA fragment. Both terminals of the isolated DNA fragment was blunted by using DNA Blunting Kit (Takara, Code No. 6025) and the DNA fragment was inserted into the SwaI site of cosmid pAxcw. The obtained cosmid pAd-CDK4 and DNA-TPC (terminal peptide complex) derived from human adenovirus type 5 were co-tranfected to HEK293 cells. The recombinant adenovirus Ad-CDK4 was obtained by in vitro recombination in 293 cells.

2) Preparation of Ad-D1NLS

The cyclin D1/NLS plasmid comprising a cyclin D1 gene attached with nucleotide sequences encoding nuclear localization signals (NLS) was constructed by ligation of the mouse cyclin D1 fragment from pRSV-cyclin D1 (refer to aforementioned Matsushime, H. et al.) and NLS from pEF1myc/nuc plasmid (Invitrogen Corp.). Namely, plasmid pEF/myc/nuc was digested with restriction enzymes NcoI and XhoI, and the first DNA fragment of approximately 5.5 kb in length was prepared using 1.0% agarose gel electrophoresis and QIAquick Gel Extraction Kit (QIAGEN Cat. No. 28704). Next, plasmid pRSV-cyclinD1 was digested with restriction enzyme NcoI, and the second 603 bp DNA fragment was prepared by the same method. Further, the third DNA fragment encoding C-terminal region of mouse cyclin D1 was prepared by polymerase chain reaction (PCR) using the following two primers and plasmid pRSV-cyclinD1 as a template.

```
NcoI primer:
                                         (SEQ ID No. 4)
5' ACCCTCCATGGTAGCTGCTGGGA 3',
and XhoI primer:
                                         (SEQ ID No. 5)
5' TGATCTCGAGGTCGATGTCCACATCTCGCACGT 3'.
```

These three DNA fragments were ligated by using DNA Ligation Kit (Takara Code No. 6022), and constructed a plasmid comprising nucleotide sequences encoding nuclear localization signals (NLS) derived from SV40 large T antigen in triplicate at the C-terminal region of mouse cyclin D1 gene. From this plasmid, a DNA fragment was excised by restriction enzymes PmaCI and SmaI, and inserted into the SwaI site of cosmid pAxcw as described above to prepare the recombinant adenovirus (Ad-D1NLS) using Adenovirus Expression Vector Kit (Takara Code No. 6150). This recombinant adenovirus Ad-D1NLS comprises mouse cyclin D1 gene attached with nucleotide sequences encoding said NLS between the CAG promoter (chick β-actin promoter+cytomegalovirus enhancer) and the polyadenylation signal of rabbit β-globin gene in DNA sequence of adenovirus deleted E1 and E3 genes.

3) Preparation of Virus Stock Solution

The 293 cells were previously cultured in each of two 6 cm dishes coated with collagen. Each 4 μg of Ad-CDK4 and Ad-D1NLS prepared above 1) and 2) was mixed with 2.5 μl of the restriction enzyme treated DNA-TPC (component of Takara Adenovirus Expression Vector Kit), and transfected to the 293 cells cultured in 6 cm dish by lipofection method respectively (FUGENE™6 Transfection Reagent, Roche cat#1814443 was used). On the following day, the cells were detached, and the recovered cell suspensions were re-inoculated on the 96 well plates coated with collagen. After 7 to 15 days, the virus grew and the cells were killed in several wells. From each of the wells in which the cells completely died, the culture medium was collected into a sterilized tube, and freeze thawed 6 times repeatedly. The supernatants after the centrifugal separation at 5000 rpm for 5 minutes, were stored at −80° C. as a first virus stock solution. 10 μl of the first virus stock solution were infected to the 293 cell cultivated in a 24 well plate coated with collagen, and collected the killed cell/media after 3 to 4 days in a sterilized tube. Freezing and thawing was repeated 6 times, and centrifuged at 5000 rpm for 5 minutes to recover the supernatant and stored at −80° C. as a second virus stock solution. 15 μl of the second virus stock solution was infected to the 293 cell cultivated in a 25 cm$^3$ bottle coated with collagen, and collected the killed cell/media after 3 to 4 days in a sterilized tube. The virus was released from the cell by freezing and thawing, or homogenizing the cell by sealed sonicator, and centrifuged at 3000 rpm for 10 minutes at 4° C. to recover the supernatant and stored at −80° C. as a third virus stock solution. 50 μl of the third virus stock solution was infected to the 293 cell cultivated in a 75 cm$^3$ bottle coated with collagen, and collected the killed cell/media after 3 to 4 days in a sterilized tube. The virus was released from the cell by freezing and thawing, or homogenizing the cell by sealed sonicator, and centrifuged at 3000 rpm for 10 minutes at 4° C. to recover the supernatant and store at −80° C. as a fourth virus stock solution. The titer of the fourth virus stock solution was determined by plaque assay with the 293 cell, and found that it was in the range from $10^9$ to $10^{11}$ pfu/ml constantly.

Example 2

Preparation of Cardiomyocytes and Infection of the Recombinant Adenovirus

Cardiomyocytes from 1- or 2-day post-natal Sprague-Dawley (SD) rats were isolated and subjected to Percoll gradient centrifugation for recovering the layer (fraction) of cardiomyocytes to suspend in MEM (minimum essential medium, Sigma, Cat. M-4655) containing 5% calf serum (Tamamori, M. et al., Am. J. Physiol. 275, (Hert Cirs. Physiol. 44), H2036-H2040 (1988)). We routinely obtained cultures in which more than 95% of the cells are cardiomyocytes as assessed by immunostaining with the mouse monoclonal anti-sarcomeric actin antibody (Dakopatts, Denmark). Neonatal rat cardiomyocytes in culture were incubated in Eagle's minimum essential medium (MEM) (Flow Laboratories) with 5% FCS (Flow Laboratories) for 24 hours. The next day, the culture medium replaced with serum-free MEM and cells were further incubated for 24 hours before virus infection. The cells were incubated with one or more than two of the recombinant adenoviruses prepared in Example 1. Cells were infected with each recombinant adenovirus (100 pfu/cell), and cultured for various periods. Fibroblast REF52 cells were prepared as controls.

Example 3

Analysis of the Gene Expression in Cardiomyocytes by Western, Kinase Assays and Immunofluorescence Staining Various growth stimulators and/or recombinant adenoviruses prepared in Example 1 were used to stimulate rat cardiomyocytes prepared in the method of Example 2. Whole cell extract, cytoplasmic extract and nuclear extract from the cell cultivated in various periods after virus infection, were purified as follows. Cells on the culture dishes were collected by cell scraper after washing with ice-cold (4° C.) PBS (Phosphate buffered saline), and then centrifuged to discard the supernatant. The obtained pellets were washed again with a small amount of PBS, and then transferred to an eppendorf tube of 1.5 ml volume. To the cell pellets, ten volumes of ice-cold (4° C.) Lysis buffer (50 mM HEPES (pH7.9), 150 mM NaCl, 0.1 mM EDTA, 0.1 mM EGTA, 0.1% NONIDET P-40, 0.4 mM NaF, 0.4 mM $Na_2VO_4$, 10% glycerol) was added, followed by pipetting on ice and mixing for 15 seconds by vortex mixer, and then stood on ice for 30 minutes. After that, the mixture was centrifuged at 15,000 rpm for 10 minutes at 4° C., and the supernatant was stored as the whole cell extract (rapidly frozen by liquid nitrogen and stored at −80° C.).

The cytoplasmic extract and the nuclear extract were fractionated as follows. Cells on the culture dishes were collected by cell scraper after washing with ice-cold (4° C.) PBS, and then centrifuged to discard the supernatant as in the above case. The obtained pellets were washed again with small amount of PBS, and then transferred to an eppendorf tube of 1.5 ml volume. To the cell pellets, five volumes of ice-cold Buffer A (10 mM HEPES (pH7.9), 1.5 mM $MgCl_2$, 10 mM KCl, 0.5 mM DTT) was added, followed by pipeting on ice and mixing for 15 seconds by vortex mixer, and then stood on ice for 10 minutes. NONIDET P-40 was further added to 0.2% in final concentration, mixed by vortex mixer and stood on ice for 5 minutes. Finally, the mixture was centrifuged at 5,000 rpm for 5 minutes, and the supernatant was stored as the cytoplasmic extract (rapidly frozen by liquid nitrogen and stored at −80° C.). The pellets were suspended in equal volume of Buffer C (20 mM HEPES (pH7.9), 25% glycerol, 0.42M NaCl, 1.5 mM $MgCl_2$, 0.2 mM EDTA), and pipetted. After mixing by vortex mixer for 15 seconds, the mixture was stood on ice for 30 minutes. Finally, the mixture was centrifuged at 15,000 rpm for 10 minutes, and the supernatant was stored as the nuclear extract (rapidly frozen by liquid nitrogen and stored at −80° C.). Incidentally, each of the above Lysis buffer, Buffer A and Buffer C was supplemented with 1 mM DTT, 1 mM PMSF, 1 μg/ml aprotinin, 1 μg/ml leupeptin, 1 μg/ml pepstatin (each was purchased from Sigma) just before use.

The protein concentration of each sample extracted by the above method was corrected as each sample was extracted from the same number of cells. Namely, the proteins extracted from $1\times10^6$ cells/each sample were electrophoresed on 6% or 1% SDS-PAGE Gel, and then the gel was transferred to nitrocellulose membrane which was further soaked in PBS containing 5% skim milk, 0.2% Tween20 and shaken for one hour (blocking). To this solution, the mouse monoclonal anti-cyclin D1 antibody (Ab-3; Oncogene science), the mouse monoclonal anti-RB antibody (14001A Pharmingen), the rabbit polyclonal anti-cyclin A antibody (SC-751; Santa Cruz Biotechnology), the rabbit polyclonal anti-cyclin E antibody (SC-481; Santa Cruz Biotechnology) and the rabbit polyclonal anti-CDK4 antibody (SC-260; Santa Cruz Biotechnology) were added, and the solutions were shaken for further one hour. Then, after the membrane was washed with PBS containing 5% skim milk, 0.2% Tween20 to remove these antibodies, it was reacted with the sheep anti-mouse Ig, horseradish peroxidase linked whole antibody (Amersham LifeScience; NA931) or the sheep anti-rabbit Ig, horseradish peroxidase linked whole antibody (Amersham LifeScience; NA934). The membrane was washed with PBS containing 5% skim milk, 0.2% Tween20 again, and then stained immunofluorescently using ECL kit (Western blotting detection reagents; Amersham LifeScience; RPN 2109) to analyze Western blot analysis.

Figure 1:
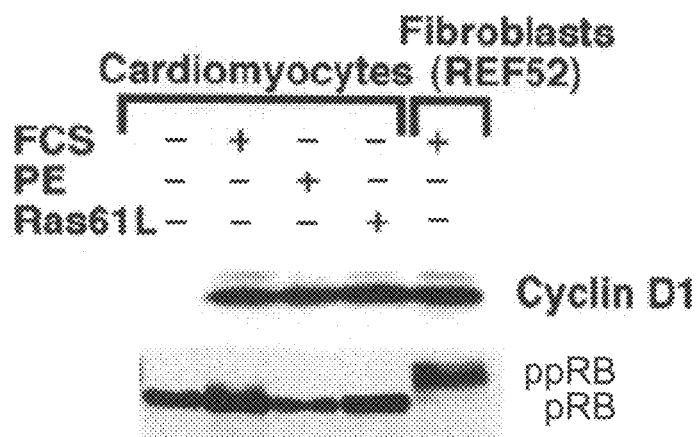

At first, the cultured neonatal cardiomyocytes were stimulated with serum as a growth stimulator, phenylephrine that is an a-adrenergic receptor agonist, and a recombinant adenovirus Ad-ras61L provided by Dr. Nevins, J. R. (Leone, G et al., Nature, 387, 422-426, (1997)) that expresses a Ras constitutively active mutant protein as a hypertrophic stimulator. The induction of cyclin D1 expression and phosphorylation of RB in response to these stimuli were analyzed by western blot analysis. FIG. 1 showed the results of electrophoresis of cell extracts stained by each antibody. Each cell was firstly infected with Ad-Ras61L or Ad-Con which is an adenovirus without Ras gene as a control, and then the culture medium was exchanged with that containing 10% serum and $10^{-6}$ M Phenylephrine (PE) or serum-free medium after 18 hours, followed by further 18 hour cultivation. As shown in FIG. 1, these stimuli induced cyclin D1 expression and CDK4 expression (data not shown). In spite of the accumulation of cyclin D1/CDK4, cyclin D1 associated kinase was not activated (data not shown), and also RB protein (pRB) was not phosphorylated, whereas RB was hyperphosphorylated state in stimulated REF52 cells, because the higher molecular weight band (ppRB) by phosphorylation was detected. In proliferating cells, RB is phosphorylated, followed by the expression of D-type cyclins. However, contrary to expectation, RB was not phosphorylated in stimulated cardiomyocytes. These data indicate that the reaction of cardiomyocytes to the growth stimuli is different from that of the growing cells in the point of the lack of RB phosphorylation.

Figure 2:
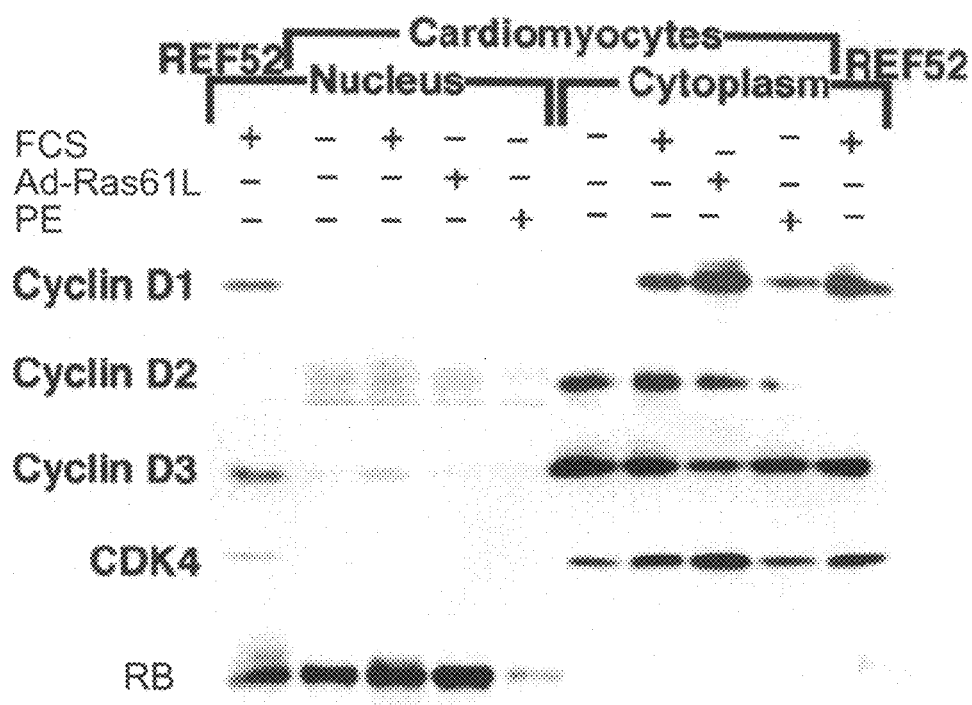

To determine the reason of the lack of RB phosphorylation in spite of the accumulation of cyclin D1, we investigated the subcellular localization of D-type cyclins and CDK4. FIG. 2 shows the results of western blot analysis of the nuclear extracts and cytoplasmic extracts from cardiomyocytes and REF52 cells. D-type cyclins and CDK4 were not expressed in nucleus and expressed only in the cytoplasmic fraction in stimulated cardiomyocytes, while cyclin D1, D3 and D4 were imported to the nucleus in stimulated REF52 cells. RB protein is in the nucleus in cardiomyocytes as well as REF52 cells.

Figure 3:
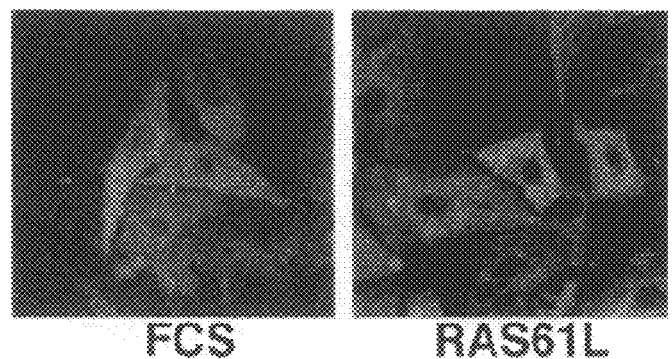

FIG. 3 are the microphotographs of cardoimyocytes stimulated by fetal calf serum or recombinant adenovirus Ad-RAS61L analyzed by immunofluorescence staining with the mouse monoclonal anti-sarcomeric actin antibody. It is observed that cyclin D1 was accumulated in cytoplasm in each cell.

Figure 4:
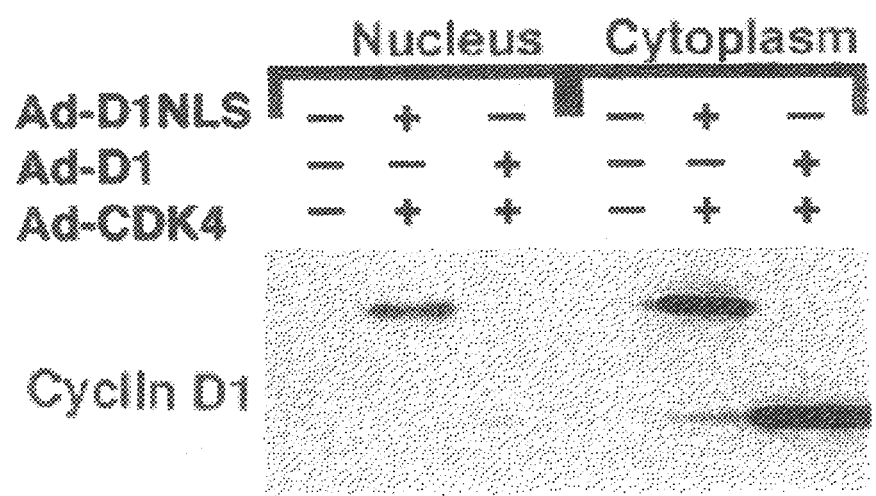
FIG. 4 shows the western blot analysis of the import of cyclin D1 to the nucleus in cardiomyocytes by the addition of nuclear localization signals.
Figure 5:
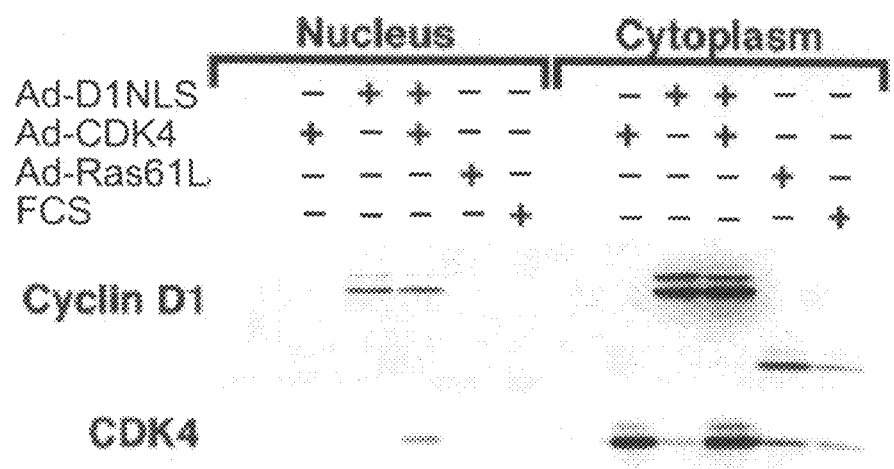
FIG. 5 shows the western blot analysis of subcellular localization of cyclin D1 and CDK4 expressed by various recombinant adenoviruses in cardiomyocytes.

Moreover, FIG. 4 shows that despite overexpression of cyclin D1 and CDK4 by using adenovirus Ad-D1 and Ad-CDK4, cyclin D1 did not accumulate in the nucleus. Therefore, we constructed adenovirus vectors coding for cyclin D with nuclear localization signals (Ad-D1NLS). As shown in FIG. 4 and FIG. 5, co-infection of Ad-D1NLS and Ad-CDK4 induced significant accumulation of cyclin D1 and CDK4 in the nucleus of cardiomyocytes. Incidentally, the adenovirus Ad-D1 which expresses human cyclin D1 was provided by Dr. Albrecht, J. of Minneapolis Medical Research Foundation (Albrecht, J. H. et al., Cell Growth & Differentiation, 10, 397-404, (1999)).

Figure 6:
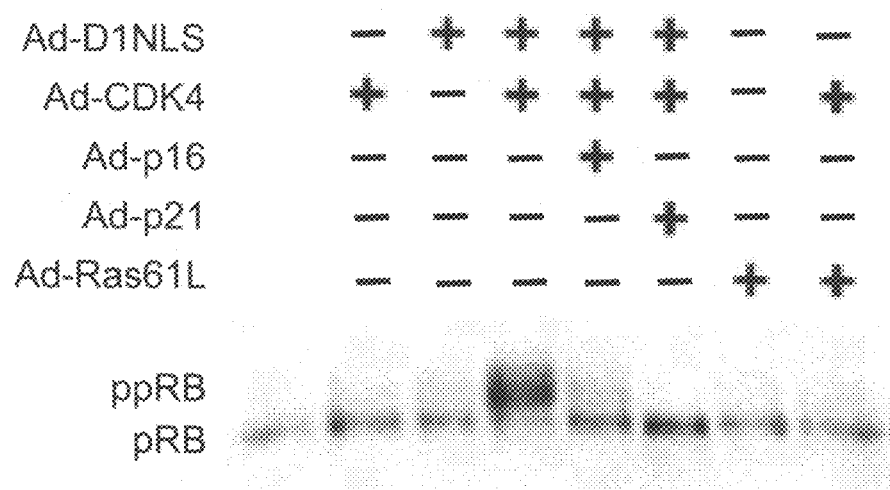
FIG. 6 shows the western blot analysis of the phosphorylation of RB in cardiomyocytes infected by various recombinant adenoviruses. ppRB: phosphorylated RB protein, pRB: RB protein.
Figure 7:
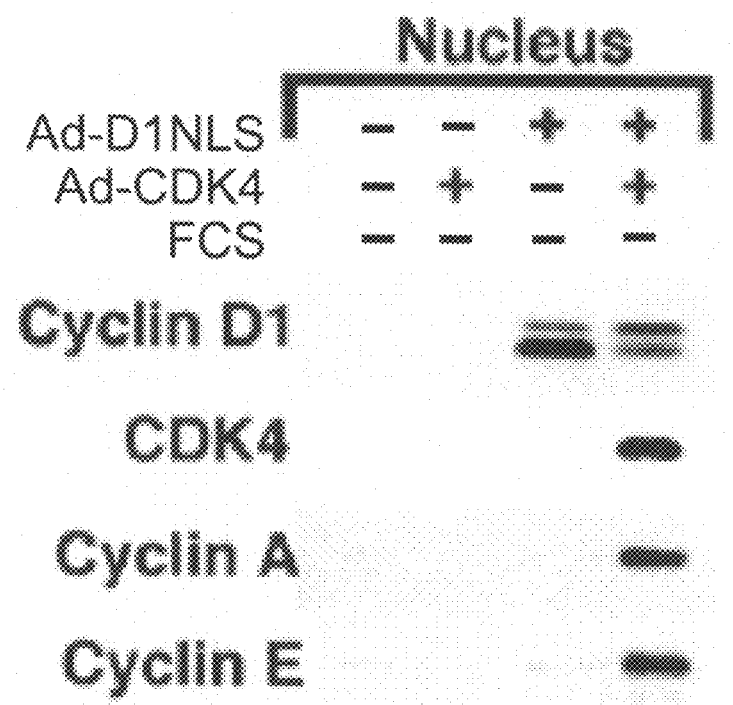
FIG. 7 shows the western blot analysis of the expression of cyclin A and cyclin E in cardiomyocytes infected by recombinant adenoviruses.

To progress from G1 to S phase, assembled cyclin D/CDK4 enter the cell nucleus where they must be phosphorylated by CDK-activating kinase (CAK) to be able to phosphorylate RB (Sherr, C. J. et al., 1999, Genes and Dev). We next investigated whether the cyclin D1 and CDK4 entered into the nucleus cause RB phosphorylation and cell cycle progression. FIG. 6 shows that co-infection of Ad-D1NLS and Ad-CDK4 causes RB phosphorylation in the nucleus of cardiomyocytes. In FIG. 6, adenovirus vectors Ad-p16 and Ad-p21 that express CDK inhibitors p16 and p21 were co-infected with the above Ad-D1NLS/Ad-CDK4, and RB phosphorylation was inhibited. Therefore, it was confirmed that the RB phosphorylation by Ad-D1NLD/Ad-CDK4 infection is dependent on the activity of the cyclin dependent kinase. FIG. 7 shows the expression of cyclin A and cyclin E that are the targets of RB/E2F in the nucleus of cardiomyocytes. These results suggest that the activity of cyclin D1/CDK4 in the nucleus possibly leads to RB phosphorylation and progression of cell cycle.

Example 4

Cell Cycle Analysis

Next, to analyze cell cycles, the recombinant adenoviruses prepared in Example 1 were infected to rat cardiomyocytes prepared in Example 2. After each of several hour incubations, cells plated on 25-mm glass coverslips were fixed with 70% ethanol and stained with propidium iodide for measurement of DNA content. Namely, cells fixed with ethanol were mixed with anti-sarcomeric actin antibody labeled by fluorescein isothiocyanate (FITC) (1:1000), and after washing with PBS, 50 μg/ml of PI, and 500 μg/ml of RNase A were added, and further incubated at room temperature for 15 minutes. The cells were detected the cell cycle position by laser scanning cytometry (LSC) (Olympus, Japan). Cardiomyocytes were identified by double staining of mouse monoclonal sarcomeric actin antibody and PI.

Figure 8A:
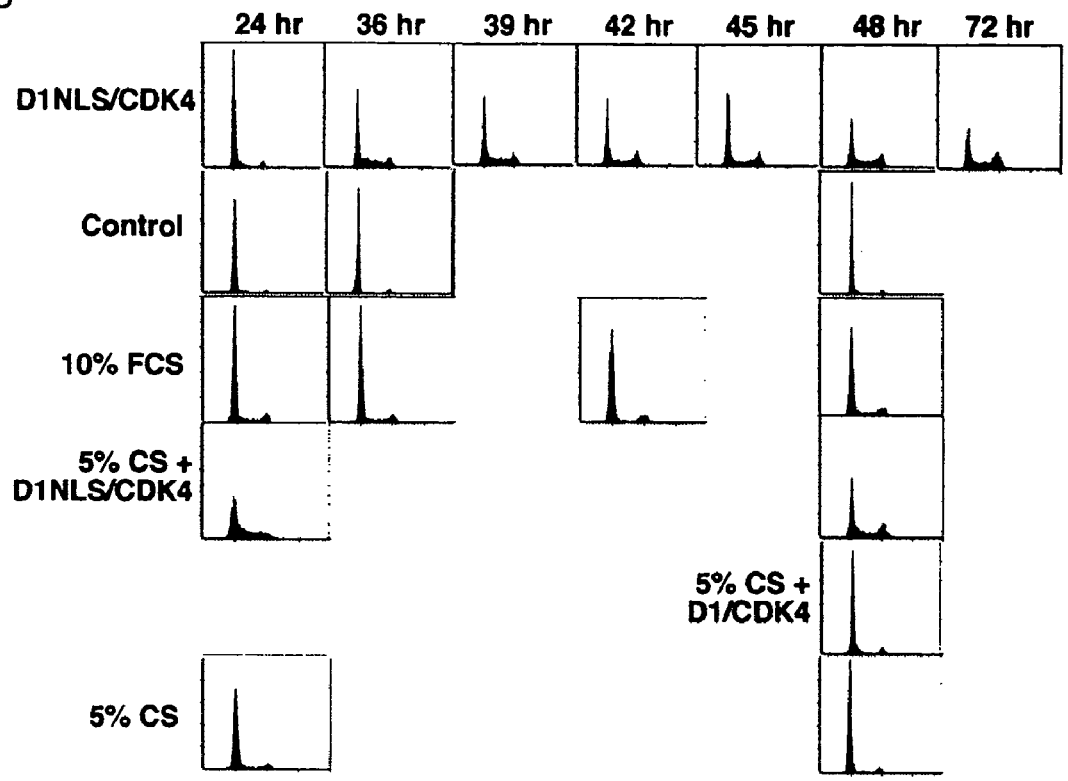
FIG. 8 shows the cell cycle analysis by laser scan cytometer (LSC) of the cardiomyocytes induced by various stimuli.

FIG. 8 shows the results of the cell cycle analysis by using laser scan cytometer (LSC). FIG. 8a shows the distribution (correlation between DNA content and cell numbers) of the cardiomyocytes induced by several viral infection or growth factors after each of incubation times. Serum starved cardiomyocytes infected with Ad-D1NLS/Ad-CDK4 were clearly induced cell cycle progression, as revealed by the increase in cells with S phase and G2 DNA content, in time dependent manner. At the presence of 5% CS, D1 NLS/CDK4 induced cell cycle faster than serum starved condition. In contrast, serum stimulation and Ad-D1/Ad-CDK4 (cyclin D1 without NLS) had no or little effect on cell cycle. Almost all of the cells cultured in 5% CS throughout after plating arrested in G1. These results suggest that D1 NLS/CDK4 enable the induction of cell cycle of post-mitotic cardiomyocytes.

Figure 8B:
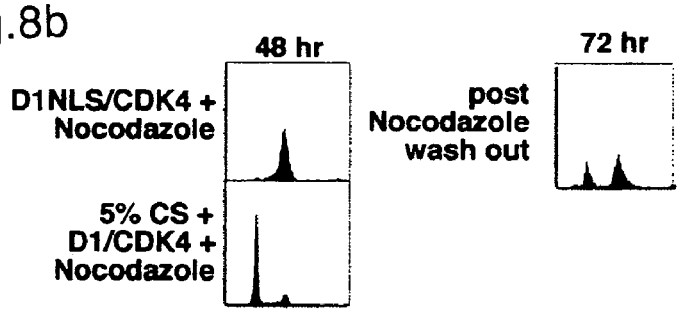

Moreover, to determine the population of cells that enter the cell cycle, we blocked the cells in G2/M phase with nocodazole (Sigma). As shown in FIG. 8b, LSC analysis revealed that approximately 95% of the cells (D1NLS/CDK4+Nocodazole) were in the G2/M fraction. Thus virtually all of the cells co-infected with AdD1NLS/AdCDK4 were entered the cell cycle. In contrast, the cardiomyocytes infected with Ad-D1/Ad-CDK4 or stimulated with serum remained in G1 phase. After washing out nocodazole from the synchronized cardiomyocytes in G2/M, these cells re-entered G1 phase. These results show that cyclin D1/CDK4 activity in the nucleus lead cardiomyocytes to proliferation at least once.

Figure 9A:
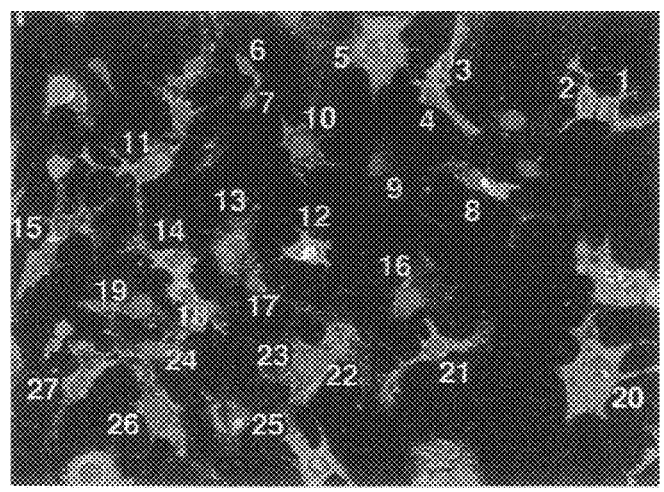
FIG. 9 shows the analysis of the mitotic cardiomyocytes visualized by LSC with confocal laser microscope.
Figure 9B:
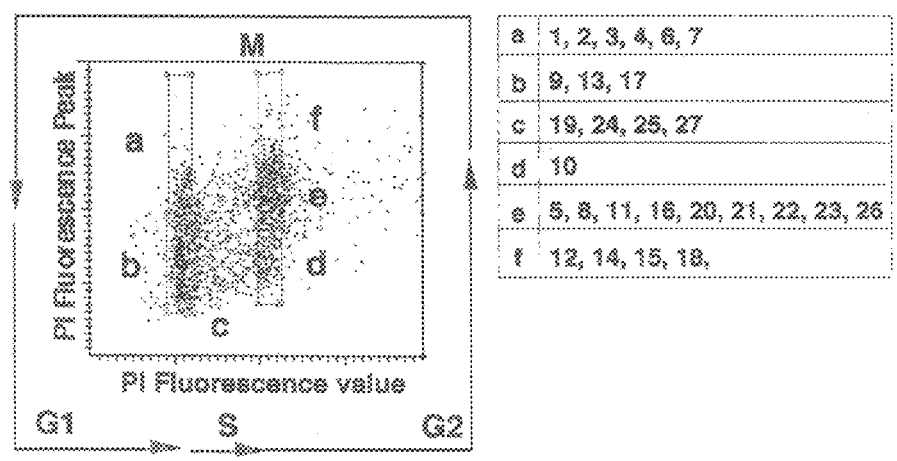

FIG. 9 shows the cardiomyocytes co-infected with Ad-D1NLS/Ad-CDK4 for 48 hours, and visualized by laser scan cytometer (LSC) with confocal laser microscope (Olympus Japan). As shown in FIG. 9a, we found many mitotic and immediately after mitotic cells. Cell cycle position of each cell was decided by DNA content measured by Pi staining (PI fluorescence value) and PI fluorescence peak (maximum value). The mitotic cells increase in their DNA content (PI fluorescence value), whereas the PI fluorescence peak of the cells immediately before or after mitosis is high (bright) due to their DNA aggregation. Based on these indications, each cell (added No.1 to 27) in the microphotograph was classified into any one of the groups (a. to f.) correlated with cell cycle positions (G1 to M phase) (FIG. 9b). As a result, cells of respective positions of G1 to M phase existed together, many mitotic and immediately after mitotic cells were observed.

Figure 10:
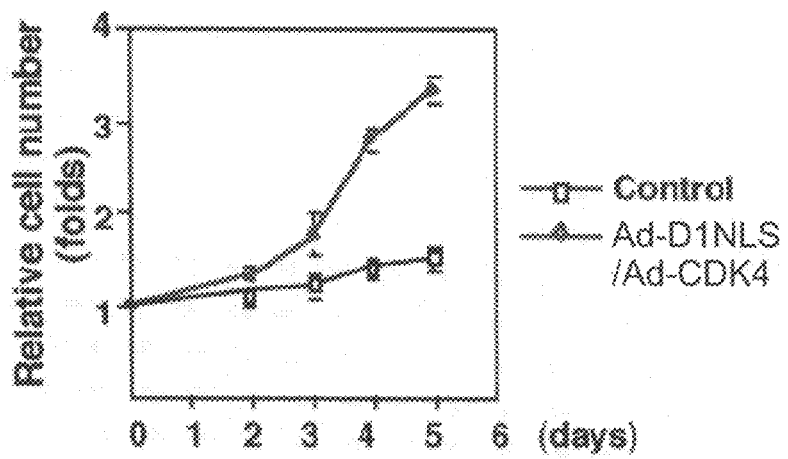
FIG. 10 shows the relative cell number counted by cell counter system, at the indicated days after viruses infection.

FIG. 10 shows the relative cell number measured by corter counter (cell number counter machine). Actually, cell number of cardiomyocytes co-infected with Ad-D1NLS/Ad-CDK4 increased in 3-times after 5 days. On the contrary, cell number of cardiomyocytes infected with only adenovirus vector as a control, did not increase.

Example 5

Study of the Possibility for Proliferating Cardiomyocytes in vivo

To test the effects of nuclear import of cyclin D1 and CDK4 on adult cardiomyocyte proliferation in vivo, two kinds of adenovirus such as Ad-D1NLS and Ad-CDK4 prepared in Example 1 and Example 2, were injected into apical region of rat hearts. Apical injections of viruses into the myocardium were performed under direct visualization after thoracotomy of Wister rats (250-300 g). As a control, an adenovirus comprising LacZ gene was also injected as described above. Four days after injections, hearts were fixed with 4% paraformaldehyde by perfusion. The sections of tissues were stained with anti-Ki-67 and anti-sarcomeric actin antibodies. Antibodies were visualized with anti-rabbit Alexa 488 or anti-mouse Alexa 568 antibodies (Molecular Probes). Images were obtained with the laser-scanning confocal image system (ZEISS LSM510) and shown in FIG. 11 in which red color indicates sarcomeric actin and green color indicates Ki-67.

Since the Ki-67 nuclear protein is expressed in proliferating cells in all phases of the cell cycle (Scholzen, T. et al., J. Cell. Physiol. 182, 311-22 (2000)), we stained sections of the infected hearts with a Ki-67 antibody to detect cells entered into the cell cycle. In the images of heart sections co-infected with the two kinds of adenovirus Ad-D1NLS and Ad-CDK4 (FIGS. 11a and 11b), the Ki-67 nuclear protein was expressed in a number of cardiomyocytes and non-cardiomyocytes. On the other hand, the expression of the Ki-67 nuclear protein was not observed in the cardiomyocytes injected with the adenovirus containing lacZ gene (FIG. 11c). These results strongly suggest that nuclear import of cyclin D1 and CDK4 could promote cell cycle entry of cardiomyocytes in adult hearts.

On the basis of these data, it was concluded that cardiomyocytes obtained the ability of proliferation by the expression of cyclin D1/CDK4 in the nucleus.

INDUSTRIAL APPLICABILITY

According to the present invention, the cell division of terminal differentiated cells is induced, and cells and tissues for transplantation can be prepared by proliferating said terminal differentiated cells. The terminal differentiated cells, in particular, such as cardiomyocytes, nerve cells, kidney cells and pancreatic cells are proliferated by themselves. The proliferated cells and tissues are expected to be used for regeneration medical care more safely and certainly compared with the case of differentiation of undifferentiated cells such as ES cells.

The invention claimed is:

1. A method for proliferating cardiomyocytes comprising: introducing nucleotide sequences coding for a D-type cyclin gene and a cyclin dependent kinase gene directly into the cardiomyocytes using a viral vector and expressing said nucleotide sequences in said cardiomyocytes,
   wherein said cyclin gene is a gene coding for cyclin D1, D2 or D3,
   wherein said cyclin dependent kinase gene is a gene coding for CDK4 or CDK6, and
   wherein a nucleotide sequence coding for a nuclear localization signal is attached to at least one of said cyclin gene or said cyclin dependent kinase gene.

2. A method for proliferating cardiomyocytes comprising: introducing nucleotide sequences coding for a D-type cyclin gene and a cyclin dependent kinase gene into cardiomyocytes in vitro using a viral vector and expressing said nucleotide sequences in said cardiomyocytes, and then cultivating said cardiomyocytes, or introducing each of said genes directly to cardiomyocytes in vivo using a viral vector and expressing said genes in said cardiomyocytes,
   wherein said cyclin gene is a gene coding for cyclin D1, D2 or D3,
   wherein said cyclin dependent kinase gene a gene coding for is CDK4 or CDK6, and
   wherein a nucleotide sequence coding for a nuclear localization signal is attached to at least one of said cyclin gene or said cyclin dependent kinase gene.

3. The method of claim 2, wherein said viral vector is an adenovirus vector.

4. The method of claim 2, wherein said genes comprising said nucleotide sequences are introduced to the cardiomyocytes in vitro, and cultivating said cardiomyocytes.

5. The method of claim 2, wherein said genes comprising said nucleotide sequences are introduced to the cardiomyocytes in vivo.

6. The method of claim 1 or 2, wherein said cyclin activates CDK4.

7. The method of claim 1 or 2, wherein said cyclin activates CDK6.

8. The method of claim 2, wherein said cyclin is D1.

9. The method of claim 1, wherein the cyclin is D2 or D3.

10. The method of claim 2, wherein the cyclin is D2 or D3.

11. The method of claim 1, wherein the cyclin dependent kinase is CDK4.

12. The method of claim 1, wherein the D-type cyclin is D1.

13. The method of claim 4, wherein the cyclin dependent kinase is CDK4.

14. The method of claim 4, wherein the D-type cyclin is D1.

15. The method of claim 4, wherein the cyclin dependent kinase is CDK4 and the D-type cyclin is D1.

16. The method of claim 5, wherein the cyclin dependent kinase is CDK4.

17. The method of claim 5, wherein the D-type cyclin is D1.

18. The method of claim 5, wherein the cyclin dependent kinase is CDK4 and the D-type cyclin is D1.

19. A method for proliferating cardiomyocytes in vitro comprising: introducing nucleotide sequences coding for a D-type cyclin and a recombinant cyclin dependent kinase gene directly into the cardiomyocytes using a viral vector and expressing said nucleotide sequences in said cardiomyocytes, and cultivating or holding said cardiomyocytes,
   wherein said cyclin gene is a gene coding for cyclin D1, D2 or D3,
   wherein said cyclin dependent kinase gene is a gene coding for CDK4 or CDK6, and
   wherein a nucleotide sequence coding for a nuclear localization signal is attached to at least one of said cyclin gene or said cyclin dependent kinase gene.

20. A method for proliferating cardiomyocytes in vivo comprising: introducing nucleotide sequences coding for a D-type cyclin gene and a cyclin dependent kinase gene directly to cardiomyocytes in vivo using a viral vector and expressing said nucleotide sequences in said cardiomyocytes,
   wherein said cyclin is cyclin D1, D2 or D3,
   wherein said cyclin dependent kinase is CDK4 or CDK6, and
   wherein a nucleotide sequence coding for a nuclear localization signal is attached to at least one of said cyclin gene or said cyclin dependent kinase gene.

21. The method of claim 1, wherein said viral vector is an adenovirus vector.

* * * * *

SEQUENCE LISTING

<160> NUMBER OF SEQ ID NOS: 5

<210> SEQ ID NO 1
<211> LENGTH: 10
<212> TYPE: PRT
<213> ORGANISM: Influenza virus

<400> SEQUENCE: 1

Ala Ala Phe Glu Asp Leu Arg Val Leu Ser
 1               5                  10

<210> SEQ ID NO 2
<211> LENGTH: 8
<212> TYPE: PRT
<213> ORGANISM: Simian virus 40

<400> SEQUENCE: 2

Pro Pro Lys Lys Lys Arg Lys Val
 1               5

<210> SEQ ID NO 3
<211> LENGTH: 16
<212> TYPE: PRT
<213> ORGANISM: Xenopus laevis

<400> SEQUENCE: 3

Lys Arg Pro Ala Ala Thr Lys Lys Ala Gly Gln Ala Lys Lys Lys Lys
 1               5                  10                  15

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: NcoI primer

<400> SEQUENCE: 4
accctccatg gtagctgctg gga                                          23

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: XhoI primer

<400> SEQUENCE: 5
tgatctcgag gtcgatgtcc acatctcgca cgt                               33